(12) United States Patent
Crawford et al.

(10) Patent No.: US 8,811,643 B2
(45) Date of Patent: *Aug. 19, 2014

(54) INTEGRATED COCHLEAR IMPLANT HEADPIECE

(75) Inventors: Scott A. Crawford, Castaic, CA (US); Douglas P. Lynch, Shepherdstown, WV (US); Carla Mann Woods, Beverly Hills, CA (US)

(73) Assignee: Advanced Bionics, Valencia, CA (US)

( * ) Notice: Subject to any disclaimer, the term of this patent is extended or adjusted under 35 U.S.C. 154(b) by 1387 days.

This patent is subject to a terminal disclaimer.

(21) Appl. No.: 12/398,058

(22) Filed: Mar. 4, 2009

(65) Prior Publication Data

US 2010/0046778 A1    Feb. 25, 2010

Related U.S. Application Data (63) Continuation-in-part of application No. 10/823,880, filed on Apr. 14, 2004, now Pat. No. 7,599,508.

(60) Provisional application No. 61/113,675, filed on Nov. 12, 2008, provisional application No. 60/469,082, filed on May 8, 2003.

(51) Int. Cl.
    *H04R 25/00* (2006.01)

(52) U.S. Cl.
    USPC ........... 381/324; 381/314; 381/315; 381/326; 381/330; 381/312; 600/25; 600/559; 607/55; 607/56; 607/57

(58) Field of Classification Search
    USPC ........ 381/328, 330, 322, 315; 600/25, 55, 56, 600/57; 607/55–57
    See application file for complete search history.

(56) References Cited

U.S. PATENT DOCUMENTS

| | | |
|---|---|---|
| 2,975,226 A | 3/1961 | Lehr |
| 3,055,990 A | 9/1962 | Sidlo |
| 3,942,535 A | 3/1976 | Schulman |
| 4,006,748 A | 2/1977 | Schulman |
| 4,041,955 A | 8/1977 | Kelly |

(Continued)

FOREIGN PATENT DOCUMENTS

| | | |
|---|---|---|
| WO | 9837926 A1 | 9/1998 |
| WO | WO 001442 A2 | 1/2000 |

(Continued)

OTHER PUBLICATIONS

Notice of Allowance Dated Jun. 13, 2012 in U.S. Appl. No. 12/397,982, with allowed claims attached.

(Continued)

*Primary Examiner* — Davetta W Goins
*Assistant Examiner* — Jasmine Pritchard
(74) *Attorney, Agent, or Firm* — Henricks, Slavin & Holmes LLP (57) ABSTRACT

An integrated headpiece for a cochlear implant system includes a microphone for outputting an audio signal; signal processing electronics for processing the audio signal; and a transmitter for transmitting a processed audio signal received from the electronics to an implanted receiver. All of the microphone, signal processing electronics, and transmitter are disposed in a common housing of the integrated headpiece. The headpiece may also be one of a set of headpieces that can be alternatively used as needed to suit power consumption requirements or environmental conditions.

7 Claims, 6 Drawing Sheets

(56) References Cited

U.S. PATENT DOCUMENTS

| | | | |
|---|---|---|---|
| 4,134,408 A | 1/1979 | Brownlee | |
| 4,352,960 A | 10/1982 | Dormer et al. | |
| 4,379,988 A | 4/1983 | Mattatall | |
| 4,532,930 A | 8/1985 | Crosby et al. | |
| 4,592,359 A | 6/1986 | Galbraith | |
| RE32,947 E | 6/1989 | Dormer et al. | |
| 4,918,736 A | 4/1990 | Bordewijk | |
| 4,947,439 A | 8/1990 | Buettner | |
| 5,279,292 A | 1/1994 | Baumann | |
| 5,314,451 A | 5/1994 | Mulier | |
| 5,411,537 A | 5/1995 | Munshi | |
| 5,411,538 A | 5/1995 | Lin | |
| 5,522,865 A | 6/1996 | Schulman | |
| 5,571,148 A | 11/1996 | Loeb | |
| 5,603,726 A | 2/1997 | Schulman et al. | |
| 5,610,494 A | 3/1997 | Grosfilley | |
| 5,626,629 A | 5/1997 | Faltys et al. | |
| 5,702,431 A | 12/1997 | Wang | |
| 5,824,022 A * | 10/1998 | Zilberman et al. | 607/57 |
| 5,906,635 A | 5/1999 | Maniglia | |
| 5,948,006 A | 9/1999 | Mann | |
| 5,949,895 A | 9/1999 | Ball et al. | |
| 6,067,474 A | 5/2000 | Schulman | |
| 6,129,753 A | 10/2000 | Kuzma | |
| 6,190,305 B1 | 2/2001 | Ball et al. | |
| 6,219,580 B1 | 4/2001 | Faltys et al. | |
| 6,246,911 B1 | 6/2001 | Seligman | |
| 6,249,704 B1 | 6/2001 | Maltan | |
| 6,265,100 B1 | 7/2001 | Saaski | |
| 6,272,382 B1 | 8/2001 | Faltys | |
| 6,275,736 B1 | 8/2001 | Kuzma et al. | |
| 6,275,737 B1 | 8/2001 | Mann | |
| 6,289,247 B1 | 9/2001 | Faltys et al. | |
| 6,304,787 B1 | 10/2001 | Kuzma | |
| 6,308,101 B1 | 10/2001 | Faltys | |
| 6,310,960 B1 | 10/2001 | Saaski | |
| 6,358,281 B1 | 3/2002 | Berrang et al. | |
| 6,394,947 B1 | 5/2002 | Leysieffer | |
| 6,415,185 B1 | 7/2002 | Maltan | |
| 6,434,429 B1 | 8/2002 | Kraus et al. | |
| 6,473,511 B1 | 10/2002 | Aceti et al. | |
| 6,496,734 B1 | 12/2002 | Money | |
| 6,556,870 B2 | 4/2003 | Zierhofer | |
| 6,560,488 B1 | 5/2003 | Crawford | |
| 6,648,914 B2 | 11/2003 | Berrang et al. | |
| 6,658,124 B1 | 12/2003 | Meadows | |
| 6,726,618 B2 | 4/2004 | Miller | |
| 6,786,860 B2 | 9/2004 | Maltan | |
| 6,807,445 B2 | 10/2004 | Baumann | |
| 6,842,647 B1 | 1/2005 | Griffith et al. | |
| 6,862,805 B1 | 3/2005 | Kuzma | |
| 6,879,695 B2 | 4/2005 | Maltan | |
| 6,879,855 B2 | 4/2005 | Schulman | |
| 7,043,303 B1 | 5/2006 | Overstreet | |
| 7,054,691 B1 | 5/2006 | Kuzma | |
| 7,149,551 B2 | 12/2006 | Kim | |
| 7,174,214 B2 | 2/2007 | Seligman | |
| 7,266,208 B2 | 9/2007 | Charvin et al. | |
| 7,266,209 B1 * | 9/2007 | House | 381/331 |
| 7,292,880 B2 | 11/2007 | Lehtonen | |
| 7,349,741 B2 * | 3/2008 | Maltan et al. | 607/57 |
| 7,386,143 B2 | 6/2008 | Easter et al. | |
| 7,599,508 B1 | 10/2009 | Lynch | |
| 7,848,817 B2 * | 12/2010 | Janzig et al. | 607/45 |
| 7,945,334 B2 | 5/2011 | Jimenez | |
| 8,107,661 B1 | 1/2012 | Lynch | |
| 8,170,253 B1 | 5/2012 | Lynch | |
| 8,270,647 B2 | 9/2012 | Crawford | |
| 8,280,524 B2 | 10/2012 | Duftner et al. | |
| 8,515,112 B2 | 8/2013 | Crawford et al. | |
| 2002/0019669 A1 * | 2/2002 | Berrang et al. | 623/10 |
| 2002/0032472 A1 | 3/2002 | Zarinetchi et al. | |
| 2002/0076071 A1 | 6/2002 | Singer | |
| 2002/0120332 A1 | 8/2002 | Law | |
| 2002/0183587 A1 | 12/2002 | Dormer | |
| 2003/0086583 A1 | 5/2003 | Maltan | |
| 2004/0073275 A1 | 4/2004 | Maltan et al. | |
| 2004/0133065 A1 * | 7/2004 | Easter et al. | 600/25 |
| 2004/0202339 A1 * | 10/2004 | O'Brien et al. | 381/312 |
| 2004/0249428 A1 | 12/2004 | Wang et al. | |
| 2005/0004629 A1 | 1/2005 | Gibson et al. | |
| 2005/0113888 A1 | 5/2005 | Jimenez et al. | |
| 2005/0159791 A1 | 7/2005 | Daly | |
| 2005/0245991 A1 | 11/2005 | Faltys et al. | |
| 2005/0251225 A1 | 11/2005 | Faltys et al. | |
| 2005/0267549 A1 | 12/2005 | Della Santina | |
| 2006/0015155 A1 | 1/2006 | Charvin et al. | |
| 2006/0052841 A1 | 3/2006 | Daly | |
| 2006/0184212 A1 | 8/2006 | Faltys et al. | |
| 2006/0190059 A1 | 8/2006 | Griffith | |
| 2007/0053534 A1 | 3/2007 | Kiratzidis | |
| 2007/0055321 A1 | 3/2007 | Gordon et al. | |
| 2007/0104342 A1 | 5/2007 | Seligman | |
| 2007/0106345 A1 | 5/2007 | Seligman | |
| 2007/0191673 A1 | 8/2007 | Ball et al. | |
| 2007/0282394 A1 | 12/2007 | Segel et al. | |
| 2008/0002834 A1 * | 1/2008 | Hochmair | 381/71.2 |
| 2008/0228243 A1 | 9/2008 | Maltan et al. | |
| 2009/0005836 A1 | 1/2009 | Chang et al. | |
| 2009/0177247 A1 | 7/2009 | Neal | |
| 2010/0036458 A1 | 2/2010 | Duftner et al. | |
| 2010/0046778 A1 | 2/2010 | Crawford et al. | |
| 2010/0046779 A1 | 2/2010 | Crawford et al. | |

FOREIGN PATENT DOCUMENTS

| | | | |
|---|---|---|---|
| WO | 0139830 A2 | 6/2001 | |
| WO | 0150816 A1 | 7/2001 | |
| WO | 03030772 A2 | 4/2003 | |
| WO | 2005062668 A1 | 7/2005 | |
| WO | WO-2005/062668 A1 | 7/2005 | |
| WO | 2005/110530 A2 | 11/2005 | |
| WO | WO-2007/124325 A2 | 11/2007 | |
| WO | 2007146773 A1 | 12/2007 | |
| WO | WO-2008/010647 A1 | 1/2008 | |
| WO | 2010017118 A1 | 2/2010 | |
| WO | WO-2010/017118 A1 | 2/2010 | |
| WO | 2010056751 A1 | 5/2010 | |
| WO | 2010056768 A1 | 5/2010 | |
| WO | 2010056770 A1 | 5/2010 | |

OTHER PUBLICATIONS

Hansaton Akustik GMBH, Product Brochures and Technical Information; Stueckenstrasse 48-D-22081, Hamburg, Germany, www.hansaton.de (2001-2002).
Office Action dated Jul. 27, 2011 in U.S. Appl. No. 12/397,982.
U.S. Appl. No. 12/546,494, filed Aug. 24, 2009.
Office Action dated Apr. 4, 2011 in U.S. Appl. No. 12/546,494.
Office Action dated Aug. 30, 2011 in U.S. Appl. No. 12/546,494.
U.S. Appl. No. 12/546,500, filed Aug. 24, 2009.
PCT International Search Report and Written Opinion dated Feb. 15, 2010 for PCT app. Ser. No. PCT/US2009/064068.
Notice of Allowance Dated Mar. 14, 2012 in U.S. Appl. No. 12/546,494, with allowed claims attached.
Office Action dated Sep. 23, 2010 in U.S. Appl. No. 12/546,494.
Office Action dated Mar. 8, 2011 in U.S. Appl. No. 12/546,500.
Office Action dated Jan. 22, 2013 in U.S. Appl. No. 13/601,992.
Office Action dated Oct. 24, 2013 in U.S. Appl. No. 13/726,817.
Office Action dated Nov. 21, 2011 in U.S. Appl. No. 12/397,982.
Notice of Allowance dated Dec. 16, 2011 is U.S. Appl. No. 12/546,500 with allowed claims attached.
Florian, John. "Technologically, cochlear implants have taken giant steps." the Hearing Journal, vol. 56, No. 4 (Apr. 2003), pp. 48.55.
"Adjustable Strength Magnet System for a Cochlear Implant Headpiece"; IP.com Publication; IPCOM000010043D; (Oct. 2002).
Jabra Corporation; "JABRA FreeSpeak(tm) BT200 Wireless Mobile Headset Users Manual"; JABRA Corporation of 9171 Towne Centre Drive, Suite 500, San Diego, California 92122; (2004); http://www.wirelessgalaxy.com/ac/jabra/BTFS_Manual.pdf.

(56) References Cited

OTHER PUBLICATIONS

Qian, et al.; "A Bluetooth-Based Wireless Phone Adapter for Cochlear Implant Users"; Department of Electrical Engineering University of Texas at Dallas; http://www.utdallas.edu/~loizou/cimplants/bluetooth.pdf; Asilomar (2001).

Qian, et al.; "A Phone-Assistive Device Based on Bluetooth Technology for Cochlear Implant Users"; IEEE Transactions on Neural Systems and Rehabilitation Engineering; (Jan. 2003); pp. 282-287.

cap. (n.d.); Webster's New Millennium™ Dictionary of English, Preview Edition (v 0.9.7); Retrieved Jan. 21, 2009; from Dictionary.com website: http://dictionary.reference.com/browse/cap.

cap; Retrieved Jan. 21, 2009; from http://www.yourdictionary.com/cap.

cap; (2009); In Merriam-Webster Online Dictionary; Retrieved Jan. 21, 2009; from http://www.merriam-webster.com/dictionary/cap.

BionicEar.com—Harmony Cochlear Implant by Advanced Bionics; "Components of a Cochlear Implant".

Welcome to Spokane Ear, Nose & Throat Clinic, P.S. Surgery Center; Retrieved Jan. 20, 2009; from http://www.spokaneent.com/cochlear_implants.html.

Cochlear Implant; Medical Articles of Interest from Garamchai.Com; Retrieved Jan. 20, 2009; from http://www.garamchai.com/DesiTrendsMedical1.htm.

Cochlear Implant Programme; Cochlear Implants, Speech Laboratory, Audiology, E . . . ; Retrieved Jan. 20, 2009; from http://www.kkrenthospital.org/surgery_cochlear.htm.

"Cochlear Implants Bring Identity Change"; Otolaryngology—Head and Neck Surgery; Breakthrough; Autumn 2004; p. 6.

UCSF—Cochlear Implant; "Implant System"; Retrieved Jan. 20, 2009; from http://cochlearimplant.ucsf.edu/p.asp?bodyid=implantsystem.

"Cochlear Implants and Children"; Advance for Audiologists; Sep./Oct. 2000; p. 26; www.advanceforAUD.com.

Cochlear implants—What is a Cochlear Implant and How Does it Work?; My Baby's Hearing; Retrieved Jan. 20, 2009; from http://www.babyhearing.org/HearingAmplification/Cochlear/whathow.asp.

House, William F.; "The AllHear Cochlear Implant System: the AllHear Device, their Manufacture, Preliminary Test Results, & the Future"; p. 1-46; Retrieved Mar. 3, 2009; from http://www.allhearcom/pdf/allhear_system.pdf.

* cited by examiner

INTEGRATED COCHLEAR IMPLANT HEADPIECE

RELATED DOCUMENTS

The present application claims priority under 35 U.S.C. §119(e) to U.S. Provisional Application No. 61/113,675, by Scott A. Crawford et al., filed on Nov. 12, 2008, and entitled "Integrated Cochlear Implant Headpiece," which application is hereby incorporated by reference in its entirety. The present application is a continuation-in-part, and claims the benefit under 35 U.S.C. §120, of U.S. application Ser. No. 10/823,880, filed Apr. 14, 2004, which claims the benefit under 35 U.S.C. §119(e) of U.S. Provisional Application No. 60/469,082, filed May 8, 2003. These applications are hereby incorporated by reference in their entireties.

Additionally, U.S. Application Ser. No. 12/397,982 filed on Mar. 4, 2009, the same day as the present application and entitled "Modular Speech Processor" is hereby incorporated by reference in its entirety.

U.S. Provisional Application No. 61/139,567, by Glen A. Griffith, filed on Dec. 20, 2008, and entitled "Cochlear Implant Systems Including Magnetic Flux Redirection Means," discloses a telemetry flux guide and techniques for using the same to direct magnetic flux away from the circuitry in a cochlear implant. This subject matter may be used in embodiments of the devices and methods disclosed in the present application to control magnetic flux within a cochlear implant device or system. Consequently, Application No. 61/139,567 is hereby incorporated by reference in its entirety.

BACKGROUND

In human hearing, hair cells in the cochlea respond to sound waves and produce corresponding auditory nerve impulses. These nerve impulses are then conducted to the brain and perceived as sound.

Hearing loss, which may be due to many different causes, is generally of two types: conductive and sensorineural. Conductive hearing loss typically occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also amenable to alleviation by surgical procedures.

Many people who are profoundly deaf, however, have sensorineural hearing loss. This type of hearing loss can arise from the absence or the destruction of the hair cells in the cochlea which then no longer transduce acoustic signals into auditory nerve impulses. Individuals with sensorineural hearing loss may be unable to derive any meaningful benefit from conventional hearing aid systems no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems or cochlear prostheses have been developed that can bypass the hair cells located in the cochlea by presenting electrical stimulation directly to the auditory nerve fibers. This leads to the perception of sound in the brain and provides at least partial restoration of hearing function. Most of these cochlear prosthesis systems treat sensorineural deficit by stimulating the ganglion cells in the cochlea directly using an implanted electrode or lead that has an electrode array. Thus, a cochlear prosthesis operates by directly stimulating the auditory nerve cells, bypassing the defective cochlear hair cells that normally transduce acoustic energy into electrical activity to the connected auditory nerve cells.

Prior to stimulating the nerve cells, the electronic circuitry and the electrode array of the cochlear prosthesis separate acoustic signals into a number of parallel channels of information, each representing a narrow band of frequencies within the perceived audio spectrum. Ideally, each channel of information should be conveyed selectively to a subset of auditory nerve cells that normally transmit information about that frequency band to the brain. Those nerve cells are arranged in an orderly tonotopic sequence, from the highest frequencies at the basal end of the cochlear spiral to progressively lower frequencies towards the apex.

A cochlear implant system typically comprises both an external unit that receives and processes ambient sound waves and a cochlear implant that receives data from the external unit and uses that data to directly stimulate the auditory nerve. A common configuration for a cochlear implant system thus involves internal components that are surgically implanted into the patient and external components that provide power and electrical signals representing environmental sound to the internal components. These external components typically include a Behind-the-Ear (BTE) processor worn on the ear or a body worn processor. These processors contain a microphone, batteries, and signal circuitry that processes the electrical signals generated by the microphone. The processors are connected to a headpiece by a cable. The headpiece receives the electrical signals through the cable and transmits them to the internal components.

In some cochlear implant systems, the cable or cables connecting the external components together can present some issues. For example, the cable may have to be routed through clothing or accommodated during hair styling. The cable may be snagged, pulled on, or tangled, causing the headpiece to fall off. Additionally, cables are considered unattractive by many patients and are susceptible to failure due to bending.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

As mentioned above, individuals with hearing loss can potentially be helped by a number of different hearing assistance devices. These assistive devices are typically worn regularly and over a significant period of each day. Consequently, any such hearing assistance device should be robust and reliable. Additionally, the hearing assistance device should be visually unobtrusive and not unduly restrict the user's activities. As explained above, cochlear implant users typically must wear at least two separate external units, a processor and a headpiece, that are connected by a cable.

The processor may be a Behind-The-Ear (BTE) processor or a body worn processor. A BTE processor typically uses a hook which attaches over the top of the outer ear and holds the BTE processor in place behind the ear of the user. The BTE processor contains a microphone, battery, and electronics. A cable attaches the BTE processor to the headpiece and conveys data signals and power to the headpiece. The headpiece is typically held in place by magnetic forces generated by a surgically implanted magnet that is a part of the internal cochlear implant.

A body worn processor is typically worn by attaching the processor to an article of clothing worn by the user. For example, a body worn processor may be tucked into a pocket or attached to a lapel. The body worn processor does not have the severe size and weight constraints that are associated with a BTE processor. Consequently, the electronics and battery capacity of the body worn processor can be significantly greater than BTE processors. Like the BTE processor, a cable attaches the body worn processor to the headpiece.

As mentioned above, the cable or cables connecting the external components together can be difficult to manage. For example, when a child wears a cochlear implant, the parent may have to take additional care in dressing the child and restrict some activities the child would otherwise enjoy in order to reduce the chances of the cable being snagged, pulled on, tangled, or broken. Additionally, the processor and cable can be visually distracting and are considered unattractive by many patients. For some patients, the BTE unit can be uncomfortable, particularly those who are sensitive to heavy objects hanging from their ears.

Accordingly, the present specification addresses these issues by describing an integrated cochlear implant headpiece that combines the external components of the cochlear system into a single unit that is worn directly over the surgically implanted receiver. The integrated cochlear implant headpiece is a head mounted, external component unit which provides a stand-alone support for the functionalities of the implanted components. This eliminates the need for a separate body worn processor or BTE processor and the connecting cable. Consequently, the integrated cochlear implant headpiece reduces the difficulties commonly associated with wearing and using a cochlear implant. Specifically, because there is no separate processor unit or connecting cable, there is no need to route a cable through clothing or hair and no possibility of snagging or damaging the cable. Additionally, the integrated cochlear implant headpiece can be significantly less visually intrusive and more user friendly. The modular nature of the integrated cochlear implant headpiece may allow for other devices to communicate with and/or be attached to the integrated cochlear implant headpiece to provide additional functionality. However, the integrated headpiece is configured to provide the basic functionality for the operation of the cochlear implant as a stand alone unit.

In some embodiments, the integrated cochlear implant headpiece may have one or more accessories which attach to the integrated headpiece and provide additional functionality. As discussed in U.S. application Ser. No. 10/823,880, of which the current application is a continuation-in-part, an assistive listening cap may magnetically attach to the top of the integrated cochlear implant. The assistive listening device may provide a variety of benefits to the patient. By way of example and not limitation, the assistive listening device may provide additional battery power; alternative antennas and circuitry for receiving audio signals via electromagnetic transmission; additional memory capacity; and/or additional signal processing capability.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Throughout the specification, a cochlear implant system which includes a Behind-The-Ear (BTE) processor and headpiece is used as an example of a typical cochlear implant system. As used in the specification and appended claims the term "headpiece" refers to an external component that is located on the head in proximity to an internal receiver, as opposed to a BTE processor or body worn processor.

Figure 1:
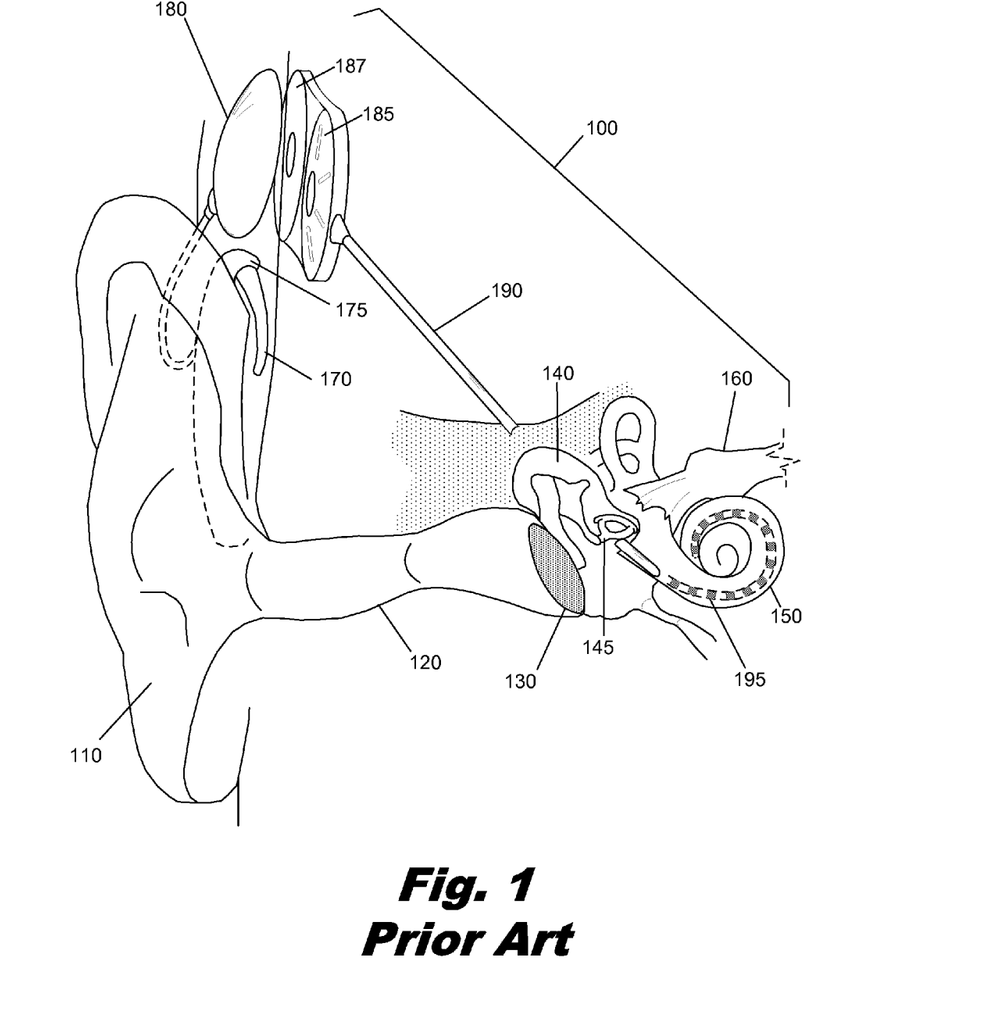
FIG. 1 is an illustrative diagram showing a cochlear implant system in use.

FIG. 1 is a diagram showing one illustrative embodiment of a cochlear implant (100) which is surgically placed within the patient's auditory system. Ordinarily, sound enters the outer ear (110) and is directed into the auditory canal (120) where the sound wave vibrates the tympanic membrane (130). The motion of the tympanic membrane is amplified and transmitted through the ossicular chain (140) which consists of three bones in the middle ear. The third bone of the ossicular chain, the stirrup (145), contacts the outer surface of the cochlea (150) and causes movement of the fluid within the cochlea (150). Cochlear hair cells respond to the fluid-borne vibration in the cochlea (150) and trigger neural electrical signals that are conducted from the cochlea (150) to the auditory cortex by the auditory nerve (160).

As indicated above, the cochlear implant (100) is a surgically implanted electronic device that provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide little benefit to persons suffering from significant sensorineural hearing loss.

Unlike hearing aids, the cochlear implant (100) does not amplify sound, but works by directly stimulating any functioning auditory nerve cells inside the cochlea (150) with electrical impulses. Cochlear prosthesis typically involves the implantation of electrodes into the cochlea. The cochlear implant operates by direct electrical stimulation of the auditory nerve cells, bypassing the defective cochlear hair cells that normally traduce acoustic energy into electrical energy.

External components of the cochlear implant system include a BTE unit (175) which contains the speech processor and has a microphone (170), a cable (177), and a transmitter (180). The microphone (170) picks up sound from the environment and converts it into electrical impulses. The speech processor within the BTE unit (175) selectively filters and manipulates the electrical impulses and sends the processed electrical signals through a cable (177) to the transmitter (180). The transmitter (180) receives the processed electrical signals from the processor and transmits them to the antenna (187) by electromagnetic induction and/or radio frequencies. In some cochlear implant systems, the transmitter (180) is held in place by magnetic attraction with the underlying antenna (187).

The internal components of the cochlear implant include an antenna (187), an internal processor (185), cochlear lead (190), and electrodes (195). The antenna (187) and internal processor (185) are secured beneath the user's skin, typically above and behind the external ear (110). As discussed above, the antenna (187) receives electromagnetic signals and power from the transmitter (180). These signals and power are transmitted using a wired connection to the internal processor (185). The internal processor (185) operates on the received signals and generates modified signals which are sent through the cochlear lead (190) to the electrodes (195). The electrodes (195) are wound through the cochlea (150) and provide direct electrical stimulation to the auditory nerve inside the cochlea (150).

The cochlear implant stimulates different portions of the cochlea (150) according to the frequencies detected by the microphone (170), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

Figures 2, 3:
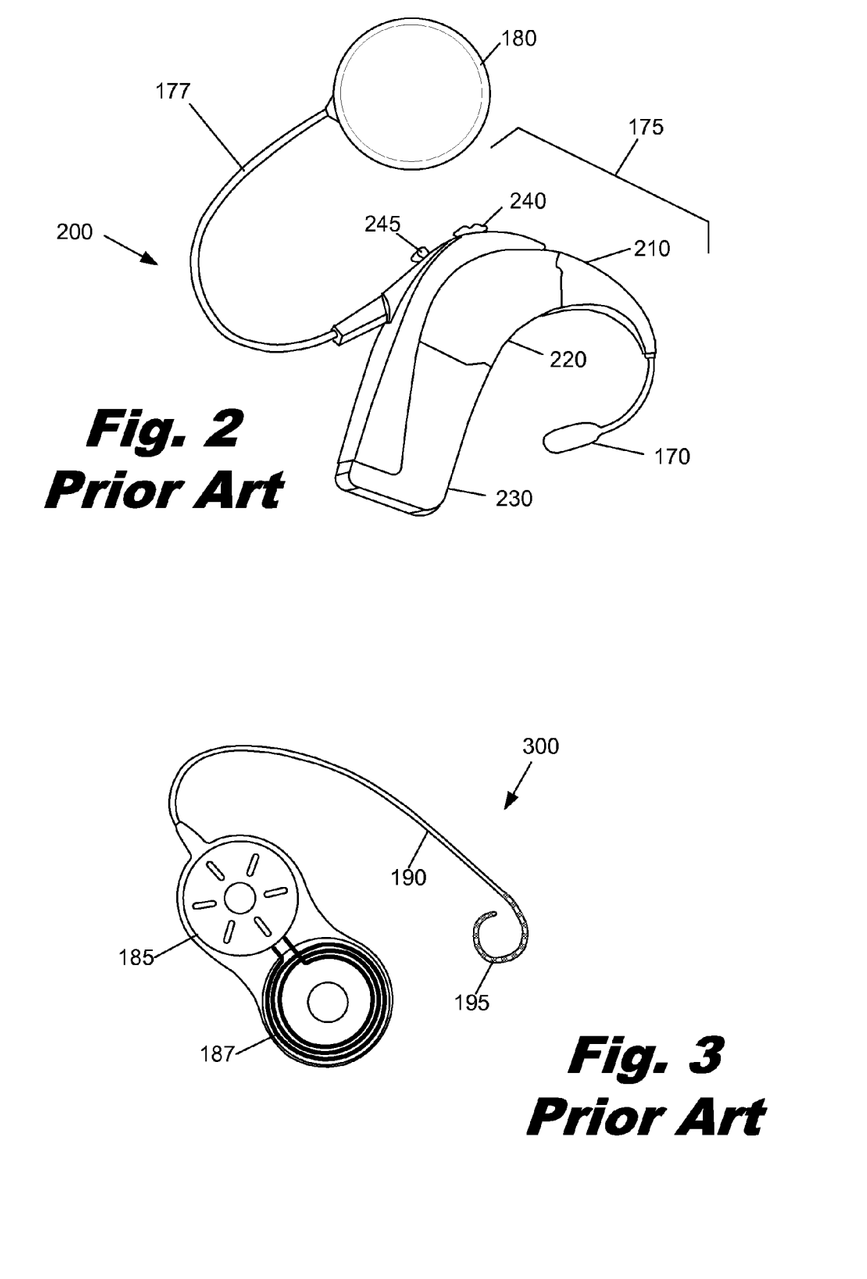
FIG. 2 is a diagram showing external components of an illustrative cochlear implant system.
FIG. 3 is a diagram showing the internal components of an illustrative cochlear implant system.

FIG. 2 is an illustrative diagram showing a more detailed view of the external components (200) of one embodiment of a cochlear implant system. External components (200) of the cochlear implant system include a BTE unit (175) which comprises a microphone (170), an ear hook (210), a speech processor (220), and a battery (230), which may be rechargeable. The microphone (170) picks up sound from the environment and converts it into electrical impulses. The speech processor (220) selectively filters and manipulates the electrical impulses and sends the processed electrical signals through a cable (177) to the transmitter (180). A number of controls (240, 245) adjust the operation of the processor (220). These controls may include a volume switch (240) and program selection switch (245). The transmitter (180) receives the processed electrical signals from the processor (220) and transmits these electrical signals and power from the battery (230) to the internal components of the cochlear implant by electromagnetic induction, radio frequencies, optical communication, or any other wireless communication technology.

FIG. 3 is an illustrative diagram showing the internal components (300) of one embodiment of a cochlear implant. These internal components (300) include an antenna (187), an internal processor (185), a cochlear lead (190), and electrodes (195). The internal components (300) of the cochlear implant are surgically implanted such that the electrodes (195) are internal to the cochlea, as shown in FIG. 1. The antenna (187) and the internal processor (185) are secured beneath the user's skin, typically above and behind the external ear, with the cochlear lead (190) connecting the internal processor (185) to the electrodes (195). As discussed above, the antenna (187) receives signals from the transmitter (180). These signals are then passed to the internal processor (185) which may perform various operations in the signals to produce modified signals which are particularly configured to be sent through the cochlear lead (190) to the electrodes (195). The electrodes (195) are wound through the cochlea and provide direct electrical stimulation to the auditory nerves inside the cochlea. This provides the user with sensory input that is a representation of external sound waves which were sensed by the microphone (170).

Figure 4:
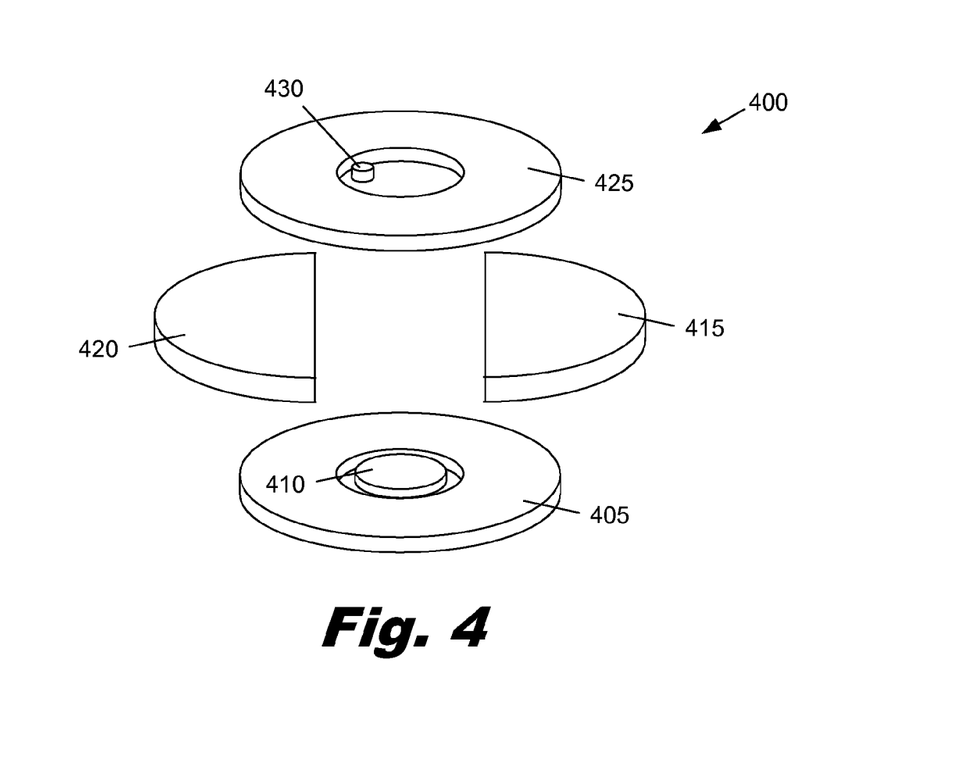
FIG. 4 is a diagram of various illustrative components which may make up an integrated headpiece, according to one embodiment of principles described herein.

FIG. 4 is an exploded view of components which may be included in an integrated headpiece (400). The integrated headpiece (400) may include a transmitter antenna (405), a magnet (410), a battery (415), electronics for audio signal processing (420), and a microphone (430). Headpiece (400) may also optionally include a receiver (425) for receiving signals from an external source.

As discussed above, the transmitter antenna (405) transmits signals to the implanted antenna (187, FIG. 3). According to one embodiment, the transmitter antenna (405) also inductively transmits power to the internal components. The magnet (410) in the center of the transmitter antenna (405) is attracted to an implanted magnetic component that is in the center of the implanted antenna (187, FIG. 3) The attraction between the magnet (410) and the implanted magnetic component holds the integrated headpiece (400) over the antenna (187, FIG. 3). The transmitter antenna (405) may also be used to receive power to charge the battery (415) when the integrated headpiece (400) is not in use. For example, the transmitter antenna (405) could be used to inductively charge the battery by placing in the transmitter antenna in proximity to a charging coil through which an alternating current is passed. The transmitter coil acts as a transformer coil and receives a portion of the energy. This energy can then be used to charge the battery within the integrated headpiece. One advantage of using inductive coupling to charge batteries is that the headpiece can be more easily sealed because there is no need for exposed conductors or connectors.

The magnet (410) may be made from any of a number of magnetic materials including, but not limited to, neodymium-iron-boron, samarium-cobalt, ticonal, alnico, ceramic, magnetic powder in a resin matrix, or other suitable material. According to one embodiment, materials which exhibit a higher magnetic strength per unit volume may be used to minimize the size of the magnet and integrated headpiece (400).

The battery (415) supplies electrical energy that is required for the function of the cochlear implant. Important considerations for a battery included in the integrated headpiece may include the energy density, total capacity of the battery, voltage, robustness, the ability to hold a charge over a long period of time, and the ability to be repeatedly charged and discharged.

By way of example and not limitation, the battery may a lithium ion battery, a polymer lithium battery, a zinc air battery or other suitable battery. Polymer lithium batteries operate using the same chemistry as conventional lithium ion batteries but contain the lithium-salt electrolyte within a solid polymer composite rather than a rigid metal case. Consequently, polymer lithium batteries can be lighter, more energy dense, and less vulnerable to physical damage. Further, polymer lithium batteries can be specifically shaped to fit the device it will power. Zinc air batteries operate by the oxidation of zinc with atmospheric oxygen. Zinc air batteries have high energy densities and are relatively inexpensive to produce. However, to operate, zinc air batteries must have direct exposure to the atmosphere, which creates challenges in using these batteries in sealed systems.

The electronics (420) may include components and functionality such as power conditioning electronics, signal processors, filters, amplifiers, receivers, switches, memory, and other electronics. The principal function of the electronics (420) is to receive an audio signal from the microphone (430) and process that signal into a signal that can be transmitted to the implanted unit to drive stimulation of the cochlea.

A number of additional components may be included in the integrated headpiece. For example, various visual indicators, such as one or more light emitting diodes, could also be included. These visual indicators could be configured to communicate information regarding the function of both internal and external components of the cochlear implant system, such as battery status, the selected program, sensitivity or volume information, and communication status between the headpiece and implanted receiver.

The integrated headpiece may optionally include a receiver (425). The receiver (425) may be any one of a variety of radio frequency (RF), WiFi, IEEE 802.11, Bluetooth®, or other receivers. These receivers can directly link the cochlear implant system to sound sources, reducing undesirable interference by other noise sources. The sound sources may include a wireless microphone, a remote control device, a cell phone, a computer, a music player, a personal digital assistant, or other device. For example, in an educational setting, teacher may wear a wireless microphone which transmits the teacher's voice over a radio frequency directly to a receiver contained within the integrated headpiece. Similarly, a Bluetooth® receiver could be connected to a stereo, cell phone, or other audio source.

A microphone (430) is also included within the integrated headpiece. The microphone (430) may reside directly on the electronics component or may be a separate component that sends electrical signals through a wired connection to the electronics. A variety of microphone types and configurations may be used. By way of example and not limitation, the microphone may use electromagnetic, capacitance change, MicroElectroMechanical Systems (MEMS) or piezoelectric mechanisms to produce an electrical signal from mechanical vibrations induced by sound. The microphone may also have one of many directional sensitivity profiles. For example, the microphone may have an omnidirectional, hemispherical, subcardioid, cardioid, or highly directional sensitivity profile.

Figure 5:
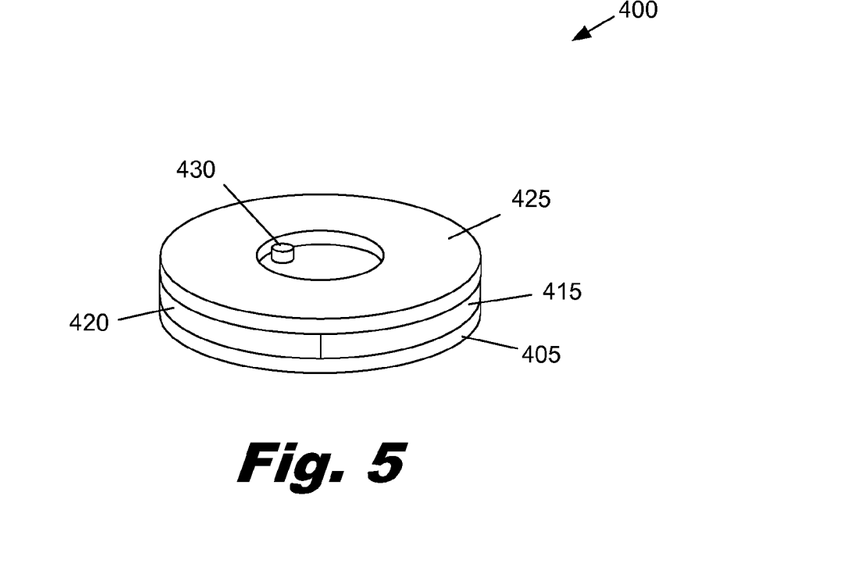
FIG. 5 is a perspective view of an illustrative integrated headpiece, according to one embodiment of principles described herein.

FIG. 5 is a diagram showing the components of the illustrative integrated headpiece (400) in an assembled configuration. As mentioned above, the integrated headpiece (400) consolidates all of the external components of the cochlear implant system in one compact unit. This eliminates cables connecting the traditional components together and the associated problems of routing the cables through clothing or the cable being snagged, pulled on, or tangled, causing the headpiece to fall off. Additionally, the integrated headpiece (400) may be more discrete than systems with multiple components. For example, the integrated headpiece (400) may be completely covered by the user's hair or hat. Further, the integrated headpiece (400) may be more robust than multiple component configurations. The integrated headpiece (400) may be much easier to seal because there is no need for external connection or cables.

Figure 6:
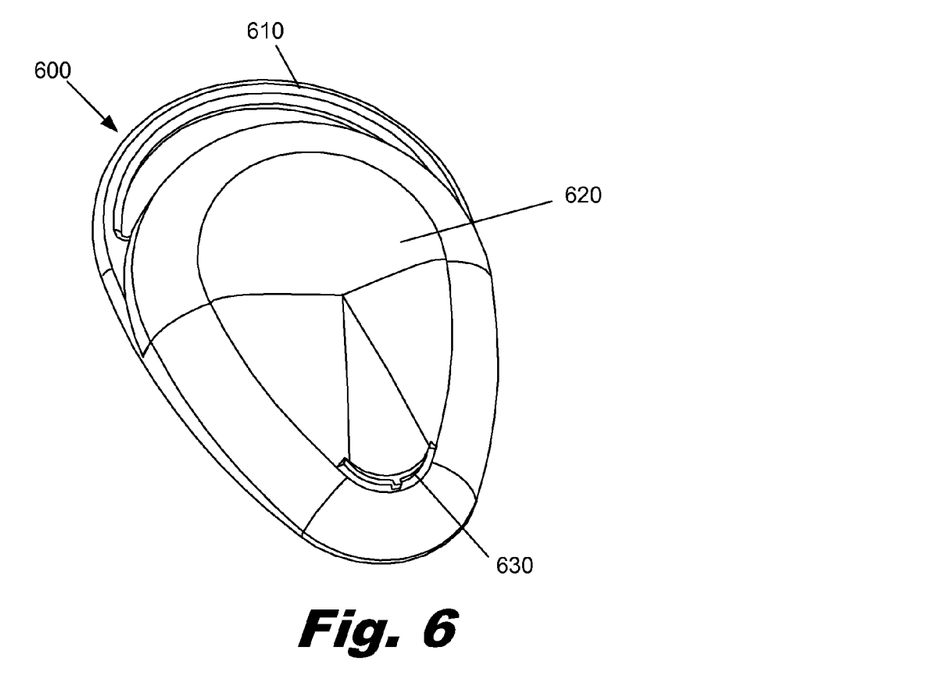
FIG. 6 is a perspective view of an illustrative integrated headpiece, according to one embodiment of principles described herein.

The components illustrated in FIGS. 4 and 5 can be configured in a number of different shapes and contained with a variety of housings. FIG. 6 shows one illustrative configuration of an integrated headpiece (600). In this illustrative embodiment, a body portion (620) contains the battery, electronics, microphone, and magnet.

A portion of the transmitter antenna (610) extends beyond the body portion (620), forming an open loop. This transmitter antenna configuration may have a number of advantages that extend beyond the visual appearance of the headpiece (600). For example, the transmitter antenna (610) may additionally serve as an inductive pick up which receives electrical energy from an exterior coil to charge the internal battery.

The exposed portion of the transmitter antenna (610) may also allow for more efficient transfer of the electrical power from the exterior coil because the exterior coil could substantially surround the transmitter antenna. In one charging configuration, the exposed portion of the transmitter antenna (610) may be inserted into a corresponding slot in a charging platform. One or more charging coils could be placed on either side of the slot. The transmitter antenna (610) would then be in very close proximity to the charging coils. Additionally, the exposed portion transmitter antenna (610) could assist in the proper positioning and retention of the integrated headpiece (600) within the charging platform.

The integrated headpiece may also have a number of other features. As mentioned above, visual indicators could be incorporated into the external shell of the integrated headpiece to allow a caretaker to visually ascertain the state and functionality of the integrated headpiece. By way of example and not limitation, the indicating features may include light emitting diodes which indicate the battery condition. For example, as the battery discharges, a light emitting diode is illuminated to indicate the need to recharge or replace the battery. This could be advantageous for a parent or teacher who can visually determine the battery level.

Similarly, the integrated headpiece may have one or more visual elements which indicate the state of the cochlear implant. For example, a light emitting diode could have a first color and illumination pattern which indicates that cochlear implant is operational. The light emitting diode could have a different color and/or illumination pattern for various malfunctions such as a malfunction of the integrated headpiece, lack of communication between the integrated headpiece and implanted receiver, or a receiver malfunction.

In the illustrative embodiment shown in FIG. 6, a switch (630) is included to allow the user to adjust the amplification of the device or to switch between a number of predetermined programs. For example, a first program may be specially adapted for personal conversations with minimal background noise, while a second program may be optimized for environments with much higher levels of background noise, such as a restaurant or crowded convention venue. A third program setting may activate a Radio Frequency (RF) receiver that is linked to a microphone worn by a teacher, lecturer, or conversationalist. By including external switches, the user can adjust the integrated headpiece in real time to suit a particular sound environment.

Figure 7:
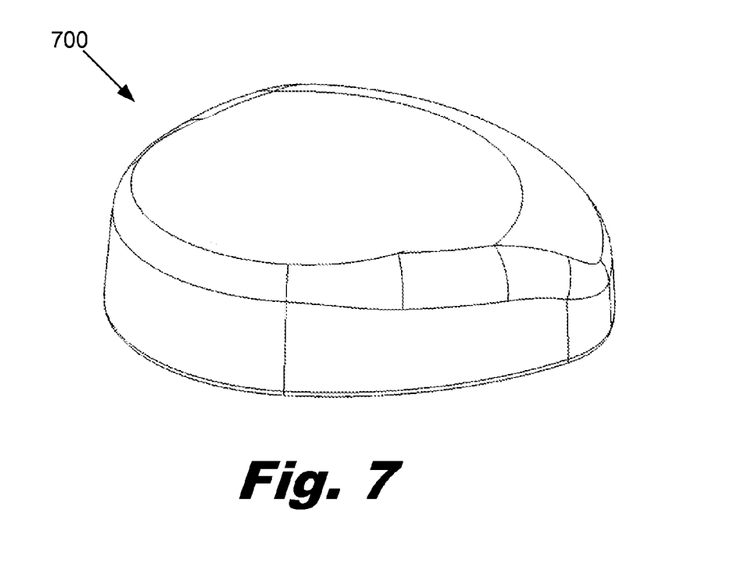
FIG. 7 is a perspective view of an illustrative integrated headpiece, according to one embodiment of principles described herein.

FIG. 7 is a perspective view of an illustrative integrated headpiece (700). In this illustrative embodiment, the exterior profile of the headpiece (700) is simplified, which may result in a more robust and inexpensive device. This common rigid housing contains the microphone, signal processing electronics, transmitter and power supply. The rigid housing maintains its shape during normal handling and provides protection for the internal components against external contaminants and impact. Additionally, external switches and visual indicators may be omitted from the headpiece. By eliminating these external features, the headpiece may be more easily constructed to be waterproof, allowing the user to walk in the rain, swim, or participate in water sports without removing the headpiece. This will allow the user to continue to receive auditory signals, thereby enhancing the user's enjoyment of the activity, ability to interact with others, and increasing the user's safety.

According to one embodiment, the headpiece may be linked via a receiver in the headpiece to an external control unit. For example, a number of controls could be incorporated into a key fob. By pressing buttons on the key fob, wireless signals could be sent to adjust the operational parameters of the integrated headpiece.

Figure 8:
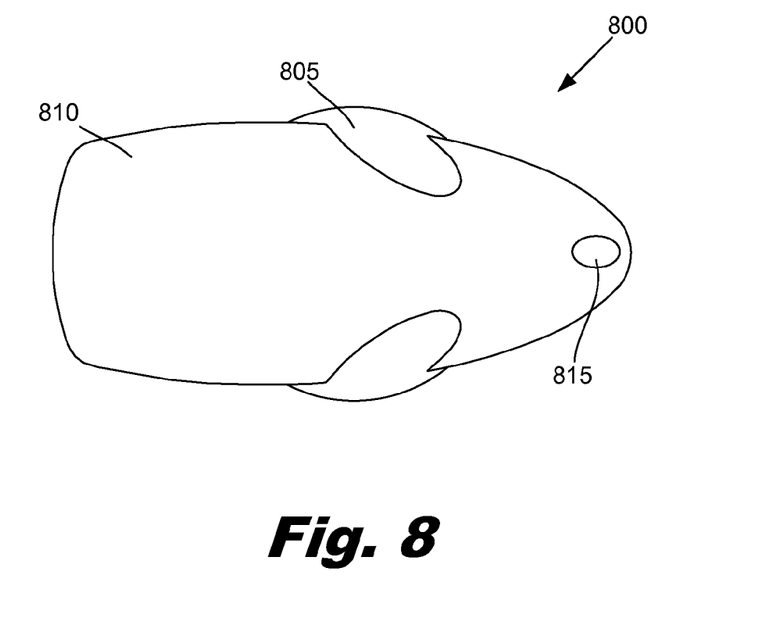
FIG. 8 is a top view of an illustrative integrated headpiece, according to one embodiment of principles described herein.

FIG. 8 is a top view of an illustrative integrated headpiece (800) with an alternative geometry. In this illustrative embodiment, the transmitter antenna may be contained within a center portion (805) of the integrated headpiece (800). Other components may be contained within the body portion (810). According to one illustrative embodiment, the integrated headpiece (800) may additionally include a directional microphone (815). Typically, omnidirectional or hemispherical microphones are used in cochlear devices to better replicate the sensitivity of the human ear. However, in some circumstances it may be beneficial to more selectively sense external sounds, thereby reducing background noise. The directional microphone (815) can be used by the patient to selectively amplify selected sound sources. According to one embodiment, the directional microphone (815) may be pointing in the same direction the patient is looking. For example, a patient may simply turn his head toward one who is speaking to point the directional microphone (815) in the speaker's direction to preferentially sense his voice.

The lower cost and ease of wearing the integrated headpiece can lead to a number of benefits. For example, the patient may have two or more integrated headpieces. While one integrated headpiece is being worn by the user, the other integrated headpiece can be recharging its battery.

Additionally or alternatively, the functionality provided by a second integrated headpiece may be different. The user can then select the integrated headpiece that is most appropriate for the situation. For example, during a social event, the user may select an integrated headpiece that is less obtrusive or complements other clothing accessories. During the course of a normal day, the user may select an integrated headpiece with a longer lifetime or with a needed receiver. For example, if the user attends school, the user may need a battery that can supply power throughout the school day and a receiver that can receive amplified/filtered signals from a wireless microphone worn by the teacher. If the user is participating in water activities, a sealed headpiece could be selected.

Figure 9:
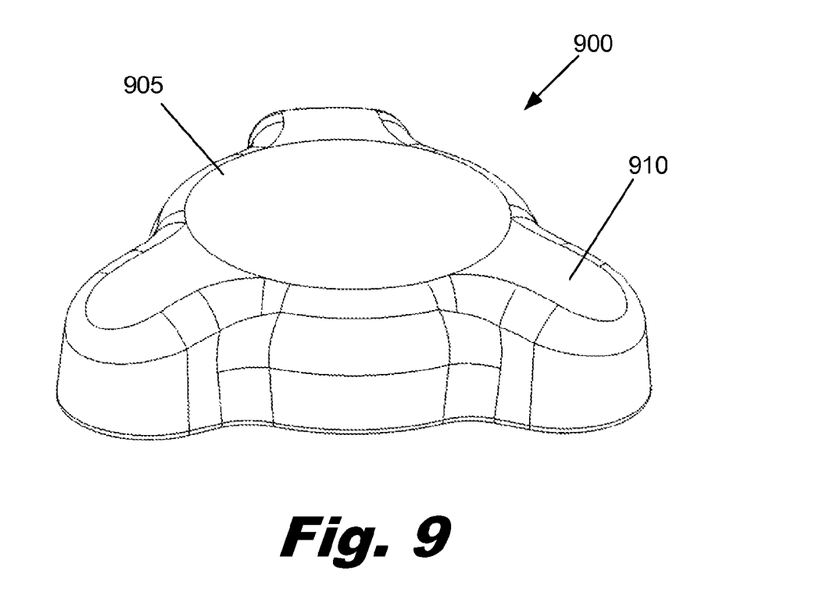
FIG. 9 is a perspective view of an illustrative integrated headpiece, according to one embodiment of principles described herein.

FIG. 9 is a perspective view of an illustrative integrated headpiece (900) with an alternative geometry. According to one embodiment, the integrated headpiece (900) has a number of lobes (910) which surround a central body portion (905). These lobes (910) may serve a number purposes including increasing the stability of the headpiece, creating a visually interesting profile, increasing the internal volume of the integrated headpiece (900), providing a shape that is adapted to a particular transmitter or receiver, or covering a lithium polymer battery which is particularly shaped to be received by the lobes (910).

Figure 10:
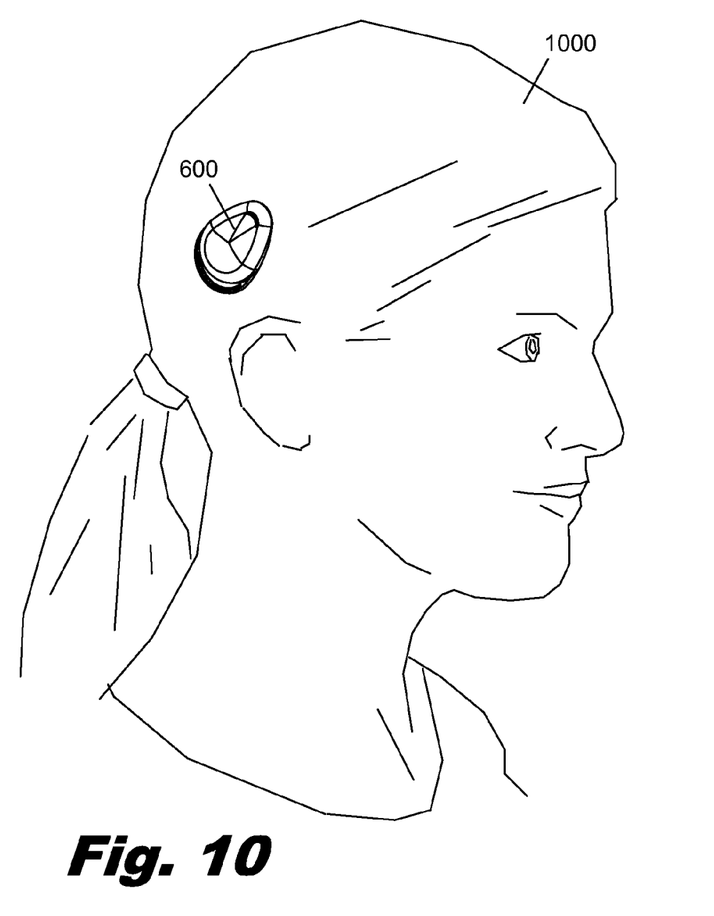
FIG. 10 is a diagram showing an illustrative integrated headpiece being worn by a user, according to one embodiment of principles described herein.

FIG. 10 shows an illustrative integrated headpiece (600) being worn by a user (1000). As discussed above, an integrated headpiece is worn over the antenna implantation site. The antenna is typically implanted above and behind the external ear as shown in FIG. 10. However, the antenna may be implanted in a variety of other locations.

If desired, the user (1000) can conceal the integrated headpiece (600) by altering her hair style or wearing a head covering such as a hat, hood, or scarf. If the user has access to a variety of integrated headpieces, the user (1000) can select the integrated headpiece that is most suited for a given activity or day. The user may carry one or more backup headpieces in a pocket, purse, or backpack. If circumstances during the day make it desirable to replace the current integrated headpiece with an alternative headpiece, the user (1000) can simply reach up, grasp the integrated headpiece (600) and remove it. A second integrated headpiece is then retrieved, oriented with the magnet side toward the head, and brought to the approximate location of the implanted antenna. As the second integrated headpiece nears the antenna location, the magnetic attraction between the two magnetic components moves the integrated headpiece into the correct location and holds the integrated headpiece in place.

Figure 11:
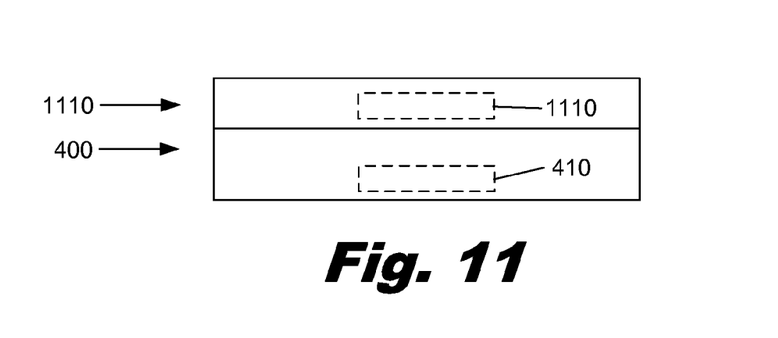
FIG. 11 is a side view of an illustrative integrated headpiece and an illustrative assistive listening device cap, according to one embodiment of principles described herein.

An integrated cochlear implant headpiece may have one or more accessories which attach to the integrated headpiece and provide additional functionality. As discussed in U.S. application Ser. No. 10/823,880, of which the current application is a continuation-in-part, an assistive listening cap (1100) may magnetically attach (note magnet 1110) to the top of the integrated cochlear implant (400) with magnet (410). The assistive listening device may provide a variety of benefits to the patient. By way of example and not limitation, the assistive listening device may provide additional battery power; alternative antennas and circuitry for receiving audio signals via electromagnetic transmission; additional memory capacity; and/or additional signal processing capability.

In sum, an integrated headpiece combines the external components of the cochlear implant system into a single unit that is worn directly over the surgically implanted receiver. This eliminates the need for a separate body worn processor or BTE processor and the connecting cable. Consequently, the integrated headpiece reduces the complexity of wearing and using a cochlear implant. The integrated headpiece eliminates the need to route a cable through clothing or hair and the possibility of snagging a cable. Additionally, the integrated headpiece can be more robust, modular, and significantly less visually intrusive than processors of conventional cochlear implant systems.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. An integrated headpiece for use with a cochlear implant, comprising:
    a microphone for outputting an audio signal;
    a headpiece magnet for attracting said headpiece to said cochlear implant;
    signal processing electronics for processing said audio signal into a processed audio signal;
    a transmitter for transmitting said processed audio signal received from said electronics to said cochlear implant; and
    an assistive listening device cap that provides additional functionality to said headpiece, said headpiece and said assistive listening device cap being respectively configured such that said assistive listening device cap can be magnetically secured to and communicate with said headpiece when said headpiece is magnetically secured to said cochlear implant;

wherein all of said microphone, headpiece magnet, signal processing electronics, and transmitter are disposed in a common rigid housing of said integrated headpiece, said integrated headpiece being configured as a stand alone, head-mounted external component which provides external functionality for operation of said cochlear implant system.

2. The headpiece of claim 1, wherein said integrated headpiece further comprises a power source, said power source supplying electrical power to said microphone, signal processing electronics and transmitter.

3. The headpiece of claim 2, wherein said power source comprises a battery.

4. An integrated headpiece for use with a cochlear implant, comprising:
- a common housing that includes a top outer surface and a bottom outer surface and is not a behind-the-ear sound processor housing;
- a headpiece magnet that is attracted to the cochlear implant;
- a microphone that outputs an audio signal;
- signal processing electronics that process the audio signal into a processed audio signal; and
- means for transmitting the processed audio signal to the cochlear implant;
- wherein all of the microphone, headpiece magnet, signal processing electronics, and means for transmitting are disposed within the common housing; and
- wherein the common housing includes a main portion and a loop that is connected to the main portion at only two locations such that an open space that extends through the top and bottom outer surfaces is defined between, and bordered on all sides by, the main portion and the loop.

5. The integrated headpiece of claim 4, further comprising:
a power source disposed within the common housing.

6. The integrated headpiece of claim 4, wherein the common housing is substantially disc-shaped.

7. An integrated headpiece for use with a cochlear implant, comprising:
- a substantially egg-shaped common housing that includes a top outer surface and a bottom outer surface and is not a behind-the-ear sound processor housing;
- a headpiece magnet that is attracted to the cochlear implant;
- a microphone that outputs an audio signal;
- signal processing electronics that process the audio signal into a processed audio signal; and
- means for transmitting the processed audio signal to the cochlear implant;
- wherein all of the microphone, headpiece magnet, signal processing electronics, and means for transmitting are disposed within the common housing; and
- wherein the common housing includes a main portion and a loop that is connected to the main portion at only two locations such that an open space that extends through the top and bottom outer surfaces is defined between, and bordered on all sides by, the main portion and the loop.

\* \* \* \* \*